(12) United States Patent
Bussolari

(10) Patent No.: US 12,350,266 B2
(45) Date of Patent: *Jul. 8, 2025

(54) FGFR2 INHIBITORS FOR THE TREATMENT OF CHOLANGIOCARCINOMA

(71) Applicant: Janssen Pharmaceutica NV, Beerse (BE)

(72) Inventor: Jacqueline Cirillo Bussolari, Skillman, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 59 days.

This patent is subject to a terminal disclaimer.

(21) Appl. No.: 18/341,023

(22) Filed: Jun. 26, 2023

(65) Prior Publication Data

US 2024/0016801 A1    Jan. 18, 2024

Related U.S. Application Data

(63) Continuation of application No. 16/616,067, filed as application No. PCT/EP2018/064523 on Jun. 1, 2018, now Pat. No. 11,707,463.

(30) Foreign Application Priority Data

Jun. 2, 2017   (EP) ..................................... 17174295
May 8, 2018   (EP) ..................................... 18171315

(51) Int. Cl.
| | |
|---|---|
| A61K 31/498 | (2006.01) |
| A61P 35/00 | (2006.01) |
| C12Q 1/6827 | (2018.01) |
| C12Q 1/6886 | (2018.01) |

(52) U.S. Cl.
CPC ............ *A61K 31/498* (2013.01); *A61P 35/00* (2018.01); *C12Q 1/6827* (2013.01); *C12Q 1/6886* (2013.01); *C12Q 2600/156* (2013.01); *G01N 2800/7028* (2013.01)

(58) Field of Classification Search
CPC .................................................. A61K 31/498
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |
| 5,882,864 A | 3/1999 | An et al. | |
| 6,218,529 B1 | 4/2001 | An et al. | |
| 11,707,463 B2* | 7/2023 | Bussolari | C12Q 1/6886 514/250 |
| 2009/0137804 A1 | 5/2009 | Ding et al. | |
| 2011/0178097 A1 | 7/2011 | Okhamafe et al. | |
| 2013/0072457 A1 | 3/2013 | Saxty et al. | |
| 2014/0322220 A1 | 10/2014 | Harrenga et al. | |
| 2015/0366866 A1 | 12/2015 | Ali et al. | |
| 2016/0090633 A1 | 3/2016 | Platero et al. | |

FOREIGN PATENT DOCUMENTS

| | | |
|---|---|---|
| WO | 2006/000420 A1 | 1/2006 |
| WO | 2006/127926 A2 | 11/2006 |
| WO | 2008/112408 A1 | 9/2008 |
| WO | 2013/076186 A1 | 5/2013 |
| WO | 2014/113729 A2 | 7/2014 |
| WO | 2016/048833 A2 | 3/2016 |
| WO | 2017/070708 A1 | 4/2017 |

OTHER PUBLICATIONS

Advanced Organic Chemistry, by Jerry March, 4th Edition, Wiley Interscience, p. More particularly, N-oxides can be made by the procedure of L. W. Deady, Syn. Comm., 1977, vol. 7, pp. 509-514.
Angerer et al., "Tissue-Specific Gene Expression: Demonstration of Tissue-Specific Expression by in Situ Hybridization.", Meth. Enzymol., 1987, vol. 152, p. 649.
Bahleda et al., "Phase 1 study of JNJ-42756493, a pan-fibroblast growth factor receptor (FGFR) inhibitor, in Patients with advanced solid tumors", Journal of Clinical Oncology, 2014, vol. 32, Issue 15, pp. 1-4.
Bartlett et al., "Technical Overview, Molecular Diagnosis of Cancer, Methods and Protocols", Second Edition, Series: Methods in Molecular Medicine, ISBN: 1-59259-760-2; Mar. 2004, pp. 77-88.
Bello et al., "E-3810 is a Potent Dual Inhibitor of VEG FR and FGFR that Exerts Antitumor Activity in Multiple Preclinical Models.", Cancer Res., Feb. 15, 2011, vol. 71, No. 4, pp. 1396-1405.
Byron et al., "The N550K/H Mutations in FGFR2 Confer Differential Resistance to PD 173074, Dovitinib, and Ponatinib ATP-Competitive Inhibitors.", Neoplasia, Aug. 1, 2013, vol. 15, No. 8, XP009172164, pp. 975-988.
Chong et al., "The landscape of targeted therapies for cholangiocarcinoma: current status and emerging targets", Oncotarget, Apr. 18, 2016, vol. 7, No. 29, XP055422802, pp. 46750-46767.
Clinical trials.gov archive: "A Study to Evaluate the Clinical Efficacy of JNJ-42756493 (Erdafitinib), A Pan-Fibroblast Growth Factor Receptor (FGFR) Tyrosine Kinase Inhibitor, In Asian Participants With Advanced Non-Small-Cell Lung Cancer, Urothelial Cancer, Esophageal Cancer or Cholangiocarcinoma"; version 16, Retrieved from https://clinicaltrials.gov/ct2/history/NCT02699606?V_16=View#StudyPageTop, retrieved on Jun. 2022, 8 Pages.
Deady, "Ring Nitrogen Oxidation of Amino Substituted Nitrogen Heterocycles with m-Chloroperbenzoic Acid", Synthetic Communications, 1977, vol. 7, No. 8, pp. 509-514.

(Continued)

Primary Examiner — Rei Tsang Shiao
(74) Attorney, Agent, or Firm — BakerHostetler

(57) ABSTRACT

Disclosed herein are methods of treating cholangiocarcinoma in a patient comprising: evaluating a biological sample from the patient for the presence of one or more FGFR mutants including at least the FGFR2 SNP C383R; and treating the patient with an FGFR inhibitor if one or more FGFR mutants including at least the FGFR2 SNP C383R are present in the sample.

20 Claims, No Drawings

(56) References Cited

OTHER PUBLICATIONS

Gallo et al., "Functions of Fibroblast Growth Factor Receptors in cancer defined by novel translocations and mutations", Cytokine and Growth Factor Reviews, Aug. 2015, vol. 26, Issue 4, pp. 425-449.
Gavine et al., "An Orally Bioavailable, Potent and Selective Inhibitor of the Fibroblast Growth Factor Receptor Tyrosine Kinase Family.", Cancer Res, Apr. 15, 2012, vol. 72, pp. 2045-2056.
International Search Report relating to PCT Patent Application No. PCT/EP2018/064523, filed on Jun. 1, 2008. Mailina Date of International Search Report: Sep. 19, 2018.
Rizvi et al., "The rise of the FGFR inhibitor in advanced biliary cancer: the next cover of time magazine?", J Gastrointest Oncol., 2016, vol. 7, No. 5, pp. 789-796.
Sambrook et al., "Molecular Cloning: A Laboratory Manual", 3rd Ed., Cold Spring Harbor Laboratory Press, 2001, pp. 1-21.
Soria et al., "Safety and activity of the pan-fibroblast growth factor receptor (FGFR) inhibitor erdafitinib in phase 1 study patients (Pts) with molecularly selected advanced cholangiocarcinoma (CCA).", Journal of Clinical Oncology, May 1, 2017, vol. 35, No. 15S, XP055423125, pp. 1-4.
Tabernero et al., "Phase I Dose-Escalation Study of JNJ-42756493, An Oral Pan-Fibroblast Growth Factor Receptor Inhibitor, in Patients With Advanced Solid Tumors", Journal of Clinical Oncology, 2015, vol. 33, No. 30, pp. 3401-3408.
Wang et al., "Antitumor effect of FGFR inhibitors on a novel cholangiocarcinoma patient derived xenograft mouse model endogenously expressing an FGFR2-CCDC6 fusion protein", Cancer Letters, 2016, vol. 380, No. 1, XP029662009, pp. 163-173.
Written Opinion of the International Searching Authority relation to PCT Patent Application No. PCT/EP2018/064523. Mailing Date of Written Opinion: Sep. 19, 2018.

* cited by examiner

FGFR2 INHIBITORS FOR THE TREATMENT OF CHOLANGIOCARCINOMA

CROSS-REFERENCE TO RELATED APPLICATIONS

This application is a continuation of U.S. patent application Ser. No. 16/616,067, filed Nov. 22, 2019, which is a U.S. National Stage Application of International Patent Application No. PCT/EP2018/064523, filed Jun. 1, 2018, which claims the benefit of EP Patent Application No. 17174295.0, filed on Jun. 2, 2017, and EP Patent Application No. 18171315.7, filed on May 8, 2018, all of which are incorporated by reference herein in their entireties and for all purposes.

TECHNICAL FIELD

Provided herein are methods of treating cholangiocarcinoma in a patient harboring one or more FGFR mutants with a fibroblast growth factor receptor inhibitor.

BACKGROUND

The identification of genetic abnormalities can be useful in selecting the appropriate therapeutic(s) for cancer patients. This is also useful for cancer patients failing the main therapeutic option (front-line therapy) for that cancer type, particularly if there is no accepted standard of care for second and subsequent-line therapy. Fibroblast growth factor receptors (FGFRs) are a family of receptor tyrosine kinases involved in regulating cell survival, proliferation, migration and differentiation. FGFR alterations including FGFR mutations and FGFR fusions or translocations have been observed in some cancers. To date, there are no approved therapies that are efficacious in patients with FGFR alterations.

SUMMARY

Disclosed herein are methods of treating cholangiocarcinoma in a patient comprising: evaluating a biological sample from the patient for the presence of one or more FGFR mutants; and treating the patient with an FGFR inhibitor if one or more FGFR mutants are present in the sample.

Disclosed herein are methods of treating cholangiocarcinoma in a patient comprising: evaluating a biological sample from the patient for the presence of one or more FGFR mutants including at least the FGFR2 SNP C383R; or one or more FGFR mutants including at least the fusion FGFR2-BICC1; or one or more FGFR mutants including at least the fusion FGFR2-CCAR1; or one or more FGFR mutants including at least the fusion FGFR2-KIAA1598; or one or more FGFR mutants including at least the fusion DTWD2-FGFR2; or one or more FGFR mutants including at least the fusion ESR2-FGFR2; or one or more FGFR mutants including at least the fusion FGFR2-MGEA5; or one or more FGFR mutants including at least the fusion FGFR2-SBNO2; or one or more FGFR mutants including at least the mutation FGFR2 C390>YS; or one or more FGFR mutants including at least the mutation FGFR2 N549K; in particular for the presence of one or more FGFR mutants including at least the FGFR2 C383R; and treating the patient with an FGFR inhibitor if one or more FGFR mutants as described above are present in the sample; in particular treating the patient with an FGFR inhibitor if one or more FGFR mutants including at least the FGFR2 SNP C383R are present in the sample.

Disclosed herein are methods of treating cholangiocarcinoma in a patient harboring the FGFR2 SNP C383R, or harboring the fusion FGFR2-BICC1; or harboring the fusion FGFR2-CCAR1; or harboring the fusion FGFR2-KIAA1598; or harboring the fusion DTWD2-FGFR2; or harboring the fusion ESR2-FGFR2; or harboring the fusion FGFR2-MGEA5; or harboring the fusion FGFR2-SBNO2; or harboring the mutation FGFR2 C390>YS; or harboring the mutation FGFR2 N549K; in particular harboring FGFR2 C383R, comprising administering a FGFR inhibitor to said patient. The patient may comprise one or more further FGFR mutants.

Disclosed herein is a FGFR inhibitor for use in the treatment of cholangiocarcinoma in a patient harboring the FGFR2 SNP C383R, or harboring the fusion FGFR2-BICC1; or harboring the fusion FGFR2-CCAR1; or harboring the fusion FGFR2-KIAA1598; or harboring the fusion DTWD2-FGFR2; or harboring the fusion ESR2-FGFR2; or harboring the fusion FGFR2-MGEA5; or harboring the fusion FGFR2-SBNO2; or harboring the mutation FGFR2 C390>YS; or harboring the mutation FGFR2 N549K; in particular harboring FGFR2 C383R. The patient may comprise one or more further FGFR mutants.

Disclosed herein is the use of a FGFR inhibitor in the manufacture of a medicament for the treatment of cholangiocarcinoma in a patient harboring the FGFR2 SNP C383R, or harboring the fusion FGFR2-BICC1; or harboring the fusion FGFR2-CCAR1; or harboring the fusion FGFR2-KIAA1598; or harboring the fusion DTWD2-FGFR2; or harboring the fusion ESR2-FGFR2; or harboring the fusion FGFR2-MGEA5; or harboring the fusion FGFR2-SBNO2; or harboring the mutation FGFR2 C390>YS; or harboring the mutation FGFR2 N549K; in particular harboring FGFR2 C383R. The patient may comprise one or more further FGFR mutants.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least the FGFR2 SNP C383R; or one or more FGFR mutants including at least the fusion FGFR2-BICC1; or one or more FGFR mutants including at least the fusion FGFR2-CCAR1; or one or more FGFR mutants including at least the fusion FGFR2-KIAA1598; or one or more FGFR mutants including at least the fusion DTWD2-FGFR2; or one or more FGFR mutants including at least the fusion ESR2-FGFR2; or one or more FGFR mutants including at least the fusion FGFR2-MGEA5; or one or more FGFR mutants including at least the fusion FGFR2-SBNO2; or one or more FGFR mutants including at least the mutation FGFR2 C390>YS; or one or more FGFR mutants including at least the mutation FGFR2 N549K; in particular for the presence of one or more FGFR mutants including at least the FGFR2 C383R, wherein the presence of one or more FGFR mutants including at least the FGFR2 SNP C383R; or one or more FGFR mutants including at least the fusion FGFR2-BICC1; or one or more FGFR mutants including at least the fusion FGFR2-CCAR1; or one or more FGFR mutants including at least the fusion FGFR2-KIAA1598; or one or more FGFR mutants including at least the fusion DTWD2-FGFR2; or one or more FGFR mutants including at least the fusion ESR2-FGFR2; or one or more FGFR mutants including at least the fusion FGFR2-

MGEA5; or one or more FGFR mutants including at least the fusion FGFR2-SBNO2; or one or more FGFR mutants including at least the mutation FGFR2 C390>YS; or one or more FGFR mutants including at least the mutation FGFR2 N549K; in particular wherein the presence of one or more FGFR mutants including at least the FGFR2 C383R is detected.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least the FGFR2 SNP C383R; or one or more FGFR mutants including at least the fusion FGFR2-BICC1; or one or more FGFR mutants including at least the fusion FGFR2-CCAR1; or one or more FGFR mutants including at least the fusion FGFR2-KIAA1598; or one or more FGFR mutants including at least the fusion DTWD2-FGFR2; or one or more FGFR mutants including at least the fusion ESR2-FGFR2; or one or more FGFR mutants including at least the fusion FGFR2-MGEA5; or one or more FGFR mutants including at least the fusion FGFR2-SBNO2; or one or more FGFR mutants including at least the mutation FGFR2 C390>YS; or one or more FGFR mutants including at least the mutation FGFR2 N549K; in particular for the presence of one or more FGFR mutants including at least the FGFR2 C383R, wherein the presence of one or more FGFR mutants including at least the FGFR2 SNP C383R; or one or more FGFR mutants including at least the fusion FGFR2-BICC1; or one or more FGFR mutants including at least the fusion FGFR2-CCAR1; or one or more FGFR mutants including at least the fusion FGFR2-KIAA1598; or one or more FGFR mutants including at least the fusion DTWD2-FGFR2; or one or more FGFR mutants including at least the fusion ESR2-FGFR2; or one or more FGFR mutants including at least the fusion FGFR2-MGEA5; or one or more FGFR mutants including at least the fusion FGFR2-SBNO2; or one or more FGFR mutants including at least the mutation FGFR2 C390>YS; or one or more FGFR mutants including at least the mutation FGFR2 N549K; in particular wherein the presence of one or more FGFR mutants including at least the FGFR2 C383R is detected.

DETAILED DESCRIPTION OF ILLUSTRATIVE EMBODIMENTS

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

The following abbreviations are used throughout the specification: FGFR (fibroblast growth factor receptor); FFPET (Formalin-Fixed Paraffin-Embedded Tissue); SNP (single nucleotide polymorphism).

As used herein, "treating" and like terms refer to reducing the severity and/or frequency of cancer symptoms, eliminating cancer symptoms and/or the underlying cause of said symptoms, reducing the frequency or likelihood of cancer symptoms and/or their underlying cause, and improving or remediating damage caused, directly or indirectly, by cancer.

"Biological samples" refers to any sample from a patient in which cancerous cells can be obtained and detection of a FGFR mutant is possible. Suitable biological samples include, but are not limited to, blood, lymph fluid, bone marrow, a solid tumor sample, or any combination thereof. In some embodiments, the biological sample can be FFPET.

FGFR Mutants

As used herein, the phrase "FGFR mutant" refers to a FGFR fusion gene, a FGFR single nucleotide polymorphism, a FGFR mutation or all of these. In an embodiment, the phrase "FGFR mutant" refers to a FGFR fusion gene, a FGFR single nucleotide polymorphism, or both. In an embodiment, the phrase "FGFR mutant" refers to a FGFR fusion gene. In an embodiment, the phrase "FGFR mutant" refers to a FGFR mutation.

"FGFR fusion" or "FGFR fusion gene" refers to a gene encoding FGFR (e.g., FGRF2 or FGFR3), or a portion thereof, and a fusion partner, or portion thereof, created by a translocation between the two genes. The presence of one or more FGFR fusion genes in a biological sample from a patient can be determined using the disclosed methods or using appropriate methods described in literature.

"FGFR single nucleotide polymorphism" (SNP) refers to a FGFR2 or FGFR3 gene in which a single nucleotide differs among individuals. A specific FGFR SNP in the methods of treatment or uses disclosed herein is FGFR2 C383R. The presence of one or more FGFR SNPs in a biological sample from a patient can be determined using the disclosed methods or using appropriate methods described in literature.

Whenever used herein FGFR2 SNP C383R or FGFR2 C383R denotes a FGFR2 mutation in which cysteine in position 383 is replaced by arginine. The terms may be used interchangeable.

FGFR Inhibitors for Use in the Disclosed Methods or Uses

Suitable FGFR inhibitors for use in the disclosed methods are provided herein.

In some embodiments, if one or more FGFR mutants including at least the FGFR2 SNP C383R are present in the sample, the cholangiocarcinoma patient can be treated with a FGFR inhibitor disclosed in U.S. Publ. No. 2013/0072457 A1 (incorporated herein by reference), including any tautomeric or stereochemically isomeric form thereof, and a N-oxide thereof, a pharmaceutically acceptable salt thereof, or a solvate thereof (suitable R groups are also disclosed in U.S. Publ. No. 2013/0072457 A1). In some aspects, for example, the patient can be treated with N-(3,5-dimethoxyphenyl)-N'-(1-methylethyl)-N-[3-(1-methyl-1H-pyrazol-4-yl)quinoxalin-6-yl]ethane-1,2-diamine (referred to herein as "JNJ-42756493" or "JNJ493" or erdafitinib):

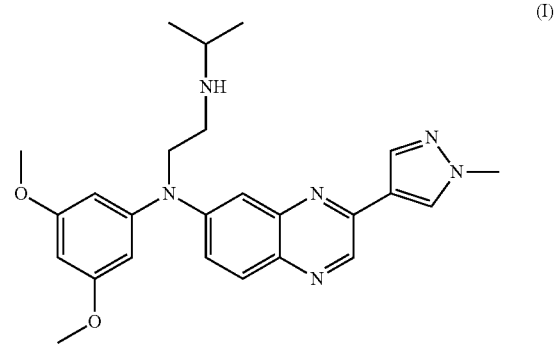 [SMILES: COc1cc(OC)cc(N(CCNC(C)C)c2ccc3ncc(-c4cnn(C)c4)nc3c2)c1]

including a N-oxide thereof, a pharmaceutically acceptable salt thereof, or a solvate thereof. In some aspects, the pharmaceutically acceptable salt is a HCl salt. In some aspects, the patient can be treated with JNJ493 base.

In some embodiments, the cholangiocarcinoma patient can be treated with a FGFR inhibitor if one or more FGFR mutants including at least the FGFR2 SNP C383R are present in the sample, wherein the FGFR inhibitor is N-[5-[2-(3,5-Di-methoxyphenyl)ethyl]-2H-pyrazol-3-yl]-4-(3,5-diemthylpiperazin-1-yl)benzamide (AZD4547), as described in Gavine, P. R., et al., AZD4547: An Orally Bioavailable, Potent, and Selective Inhibitor of the Fibroblast Growth Factor Receptor Tyrosine Kinase Family, Cancer Res. Apr. 15, 2012 72; 2045:

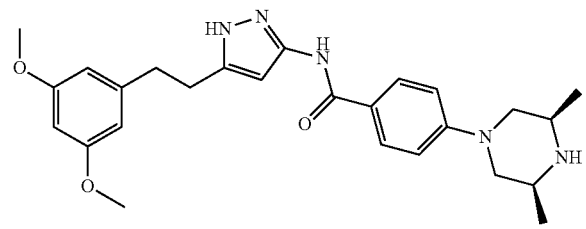

(II)

including, when chemically possible, any tautomeric or stereochemically isomeric form thereof, and a N-oxide thereof, a pharmaceutically acceptable salt thereof, or a solvate thereof In some embodiments, the cholangiocarcinoma patient can be treated with a FGFR inhibitor if one or more FGFR mutants including at least the FGFR2 SNP C383R are present in the sample, wherein the FGFR inhibitor is 3-(2,6-Dichloro-3,5-dimethoxy-phenyl)-1-{6-[4-(4-ethyl-piperazin-1-yl)-phenylamino]-pyrimid-4-yl}-1-methyl-urea (NVP-BGJ398) as described in Int'l Publ. No. WO2006/000420:

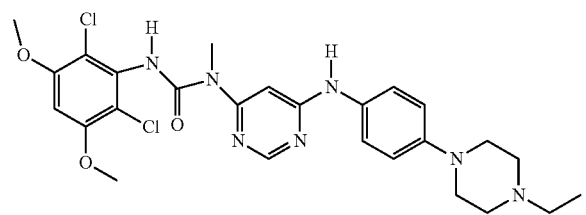

(III)

including, when chemically possible, any tautomeric or stereochemically isomeric form thereof, and a N-oxide thereof, a pharmaceutically acceptable salt thereof, or a solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is 4-amino-5-fluoro-3-[6-(4-methylpiperazin-1-yl)-1H-benzimidazol-2-yl]-1H-quinolin-2-one (dovitinib) as described in Int't Publ. No. WO2006/127926:

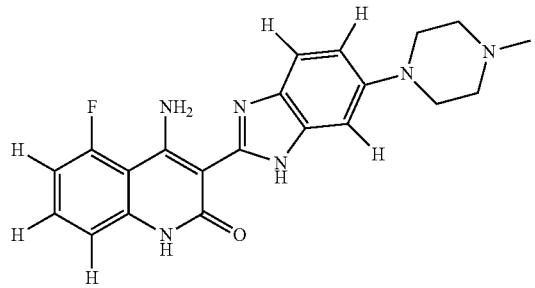

(IV)

including, when chemically possible, any tautomeric or stereochemically isomeric form thereof, and a N-oxide thereof, a pharmaceutically acceptable salt thereof, or a solvate thereof In some embodiments, the cholangiocarcinoma patient can be treated with a FGFR inhibitor if one or more FGFR mutants including at least the FGFR2 SNP C383R are present in the sample, wherein the FGFR inhibitor is 647-((1-Amino-cyclopropyl)-methoxy)-6-methoxyquinolin-4-yloxy)-N-methyl-1-naphthamide (AL3810) (lucitanib; E-3810), as described in Bello, E. et al., E-3810 Is a Potent Dual Inhibitor of VEGFR and FGFR that Exerts Antitumor Activity in Multiple Preclinical Models, Cancer Res Feb. 15, 2011 71(A)1396-1405 and Int'l Publ. No. WO2008/112408:

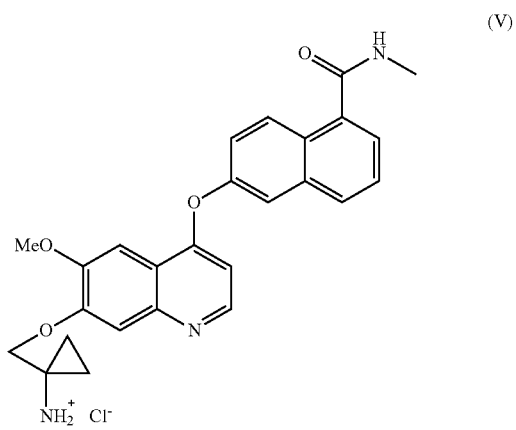 [SMILES: CNC(=O)c1cccc2cc(Oc3ccnc4cc(OCC5([NH3+])CC5)c(OC)cc34)ccc12 ; [Cl-]]

(V)

including, when chemically possible, any tautomeric or stereochemically isomeric form thereof, and a N-oxide thereof, a pharmaceutically acceptable salt thereof, or a solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is an anti-FGFR2 antibody such as that described in WO2013/076186.

Additional suitable FGFR inhibitors include BAY1163877 (Bayer), BAY1179470 (Bayer), TAS-120 (Taiho), ARQ087 (ArQule), ASP5878 (Astellas), FF284 (Chugai), FP-1039 (GSK/FivePrime), Blueprint, LY-2874455 (Lilly), RG-7444 (Roche), or any combination thereof, including, when chemically possible, any tautomeric or stereochemically isomeric forms thereof, N-oxides thereof, pharmaceutically acceptable salts thereof, or solvates thereof.

In some embodiments, the cholangiocarcinoma patient can be treated with a FGFR inhibitor if one or more FGFR mutants including at least the FGFR2 SNP C383R are present in the sample, wherein the FGFR inhibitor is BAY1163877 (Bayer), including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is BAY1179470 (Bayer), including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is TAS-120 (Taiho), including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is ARQ087 (ArQule), including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is ASP5878 (Astellas), including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is FF284 (Chugai), including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is FP-1039 (GSK/FivePrime), including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is Blueprint, including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is LY-2874455 (Lilly), including, when chemically possible, any tautomeric or stereochemically isomeric form thereof, N-oxide thereof, pharmaceutically acceptable salt thereof, or solvate thereof.

In some embodiments, the cholangiocarcinoma patient can be treated with a FGFR inhibitor if one or more FGFR mutants including at least the FGFR2 SNP C383R are present in the sample, wherein the FGFR inhibitor is RG-7444 (Roche), including, when chemically possible, any tautomeric or stereochemically isomeric form thereof, N-oxide thereof, pharmaceutically acceptable salt thereof, or solvate thereof.

Salts can be synthesized from a parent compound that contains a basic or acidic moiety by conventional chemical methods such as methods described in Pharmaceutical Salts: Properties, Selection, and Use, P. Heinrich Stahl (Editor), Camille G. Wermuth (Editor), ISBN: 3-90639-026-8, Hardcover, 388 pages, August 2002, which is incorporated herein by reference. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The FGFR inhibitors for use in the disclosed methods may exist as mono- or di-salts depending upon the pKa of the acid from which the salt is formed.

Acid addition salts may be formed with a wide variety of acids, both inorganic and organic. Examples of acid addition salts include salts formed with an acid including, but not limited to, acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R^{2+}$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds contain an amine function, these may form quaternary ammonium salts, for example by reaction with an alkylating agent according to methods well known to the skilled person. Such quaternary ammonium compounds are within the scope of the disclosed compounds. Compounds containing an amine function may also form N-oxides. A reference herein to a compound that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

As used herein, the term "solvate" means a physical association of the compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include the disclosed compounds in combination with water, isopropanol, ethanol, methanol, DMSO, ethyl acetate, acetic acid, ethanolamine and the like. The compound may exert its biological effects while in solution.

Solvates are well known in pharmaceutical chemistry. They can be important to the processes for the preparation of a substance (e.g. in relation to their purification), the storage of the substance (e.g. its stability) and the ease of handling of the substance, and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed are any complexes (e.g. inclusion complexes or clathrates with compounds such as cyclodextrins, or complexes with metals) of the FGFR inhibitor.

Furthermore, the compound may have one or more polymorph (crystalline) or amorphous forms.

The compounds include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment, the compounds contain no radioactive isotopes. Such compounds are preferred for therapeutic use. In another embodiment, however, the compound may contain one or more radioisotopes. Compounds containing such radioisotopes may be useful in a diagnostic context.

In some embodiments, the cholangiocarcinoma patient is treated with a FGFR inhibitor if one or more FGFR mutants including at least the FGFR2 SNP C383R are present in the sample, wherein the FGFR inhibitor is N-(3,5-dimethoxyphenyl)-N'-(1-methylethyl)-N-[3-(1-methyl-1H-pyrazol-4-yl)quinoxalin-6-yl]ethane-1,2-diamine (referred to herein "JNJ-42756493"), or a pharmaceutically acceptable salt thereof or a solvate thereof. In an embodiment the FGFR inhibitor is JNJ-42756493 base.

Methods of Treating Cancer in a Patient

Disclosed herein are methods of treating cholangiocarcinoma in a patient comprising: evaluating a biological sample from the patient for the presence of one or more FGFR mutants including at least the FGFR2 SNP C383R; and treating the patient with an FGFR inhibitor if one or more FGFR mutants including at least the FGFR2 SNP C383R are present in the sample. In an embodiment, the FGFR inhibitor is erdafitinib.

Disclosed herein are methods of treating cholangiocarcinoma in a patient harboring the FGFR2 SNP C383R comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring the FGFR2 SNP C383R. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring the FGFR2 SNP C383R. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least the FGFR2 SNP C383R, wherein the presence of one or more FGFR mutants including at least the FGFR2 SNP C383R is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least the FGFR2 SNP C383R, wherein the presence of one or more FGFR mutants including at least the FGFR2 SNP C383R is detected. In an embodiment, the FGFR inhibitor is erdafitinib.

In an embodiment, erdafitinib is administered at a dose of 10 mg.

In an embodiment, erdafitinib is administered at a dose of 10 mg intermittently.

In an embodiment, erdafitinib is administered at a dose of 10 mg intermittently 7 days on/7 days off.

In an embodiment, erdafitinib is administered at a dose of 8 mg, in particular 8 mg once daily. In an embodiment, erdafitinib is administered at a dose of 8 mg, in particular 8 mg once daily, with an option to uptitrate to 9 mg depending on serum phosphate levels (e.g. serum phosphate levels are <5.5 mg/dL, or are <7 mg/dL or range from and include 7 mg/dL to ≤9 mg/dL or are ≤9 mg/dL), and depending on treatment-related adverse events observed. In an embodiment, the levels of serum phosphate for determining whether or not to up-titrate are measured on a treatment day during the first cycle of erdafitinib treatment, in particular on day 14±2 days, more in particular on day 14, of erdafitinib administration.

In an embodiment of the invention, in the methods of treatment and the uses as described herein the FGFR2 SNP C383R may be replaced by the FGFR fusion FGFR2-BICC1.

Disclosed herein are methods of treating cholangiocarcinoma in a patient comprising: evaluating a biological sample from the patient for the presence of one or more FGFR mutants including at least FGFR2-BICC1; and treating the patient with an FGFR inhibitor if one or more FGFR mutants including at least FGFR2-BICC1 are present in the sample. In an embodiment, the FGFR inhibitor is erdafitinib.

Disclosed herein are methods of treating cholangiocarcinoma in a patient harboring FGFR2-BICC1 comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring FGFR2-BICC1. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring FGFR2-BICC1. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-BICC1, wherein the presence of one or more FGFR mutants including at least FGFR2-BICC1 is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-BICC1, wherein the presence of one or more FGFR mutants including at least FGFR2-BICC1 is detected. In an embodiment, the FGFR inhibitor is erdafitinib.

In an embodiment of the invention, in the methods of treatment and the uses as described herein the FGFR2 SNP C383R may be replaced by the FGFR fusion FGFR2-CCAR1.

Disclosed herein are methods of treating cholangiocarcinoma in a patient comprising: evaluating a biological sample from the patient for the presence of one or more FGFR mutants including at least FGFR2-CCAR1; and treating the patient with an FGFR inhibitor if one or more FGFR mutants including at least FGFR2-CCAR1 are present in the sample. In an embodiment, the FGFR inhibitor is erdafitinib.

Disclosed herein are methods of treating cholangiocarcinoma in a patient harboring FGFR2-CCAR1 comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring FGFR2-CCAR1. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring FGFR2-CCAR1. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-CCAR1, wherein the presence of one or more FGFR mutants including at least FGFR2-CCAR1 is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-CCAR1, wherein the presence of one or more FGFR mutants including at least FGFR2-CCAR1 is detected. In an embodiment, the FGFR inhibitor is erdafitinib.

In an embodiment of the invention, in the methods of treatment and the uses as described herein the FGFR2 SNP C383R may be replaced by the FGFR fusion FGFR2-KIAA1598.

Disclosed herein are methods of treating cholangiocarcinoma in a patient comprising: evaluating a biological sample from the patient for the presence of one or more FGFR mutants including at least FGFR2-KIAA1598; and treating the patient with an FGFR inhibitor if one or more FGFR mutants including at least FGFR2-KIAA1598 are present in the sample. In an embodiment, the FGFR inhibitor is erdafitinib.

Disclosed herein are methods of treating cholangiocarcinoma in a patient harboring FGFR2-KIAA1598 comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring FGFR2-KIAA1598. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring FGFR2-KIAA1598. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-KIAA1598, wherein the presence of one or more FGFR mutants including at least FGFR2-KIAA1598 is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-KIAA1598, wherein the presence of one or more FGFR mutants including at least FGFR2-KIAA1598 is detected. In an embodiment, the FGFR inhibitor is erdafitinib.

In an embodiment of the invention, in the methods of treatment and the uses as described herein the FGFR2 SNP C383R may be replaced by the FGFR fusion DTWD2-FGFR2.

Disclosed herein are methods of treating cholangiocarcinoma in a patient comprising: evaluating a biological sample from the patient for the presence of one or more FGFR mutants including at least DTWD2-FGFR2; and treating the patient with an FGFR inhibitor if one or more FGFR mutants including at least DTWD2-FGFR2 are present in the sample. In an embodiment, the FGFR inhibitor is erdafitinib.

Disclosed herein are methods of treating cholangiocarcinoma in a patient harboring DTWD2-FGFR2 comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring DTWD2-FGFR2. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring FGFR2-DTWD2-FGFR2. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least DTWD2-FGFR2, wherein the presence of one or more FGFR mutants including at least DTWD2-FGFR2 is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least DTWD2-FGFR2, wherein the presence of one or more FGFR mutants including at least DTWD2-FGFR2 is detected. In an embodiment, the FGFR inhibitor is erdafitinib.

In an embodiment of the invention, in the methods of treatment and the uses as described herein the FGFR2 SNP C383R may be replaced by the FGFR fusion ESR2-FGFR2.

Disclosed herein are methods of treating cholangiocarcinoma in a patient comprising: evaluating a biological sample from the patient for the presence of one or more FGFR mutants including at least ESR2-FGFR2; and treating the patient with an FGFR inhibitor if one or more FGFR mutants including at least ESR2-FGFR2 are present in the sample. In an embodiment, the FGFR inhibitor is erdafitinib.

Disclosed herein are methods of treating cholangiocarcinoma in a patient harboring ESR2-FGFR2 comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring ESR2-FGFR2. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring ESR2-FGFR2. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least ESR2-FGFR2, wherein the presence of one or more FGFR mutants including at least ESR2-FGFR2 is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least ESR2-FGFR2, wherein the presence of one or more FGFR mutants including at least ESR2-FGFR2 is detected. In an embodiment, the FGFR inhibitor is erdafitinib.

In an embodiment of the invention, in the methods of treatment and the uses as described herein the FGFR2 SNP C383R may be replaced by the FGFR fusion FGFR2-MGEA5.

Disclosed herein are methods of treating cholangiocarcinoma in a patient comprising: evaluating a biological sample from the patient for the presence of one or more FGFR mutants including at least FGFR2-MGEA5; and treating the patient with an FGFR inhibitor if one or more FGFR mutants including at least FGFR2-MGEA5 are present in the sample. In an embodiment, the FGFR inhibitor is erdafitinib.

Disclosed herein are methods of treating cholangiocarcinoma in a patient harboring FGFR2-MGEA5 comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring FGFR2-MGEA5. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring FGFR2-MGEA5. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-MGEA5, wherein the presence of one or more FGFR mutants including at least FGFR2-MGEA5 is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-MGEA5, wherein the presence of one or more FGFR mutants including at least FGFR2-MGEA5 is detected. In an embodiment, the FGFR inhibitor is erdafitinib.

In an embodiment of the invention, in the methods of treatment and the uses as described herein the FGFR2 SNP C383R may be replaced by the FGFR fusion FGFR2-SBNO2.

Disclosed herein are methods of treating cholangiocarcinoma in a patient comprising: evaluating a biological sample from the patient for the presence of one or more FGFR mutants including at least FGFR2-SBNO2; and treating the patient with an FGFR inhibitor if one or more FGFR mutants including at least FGFR2-SBNO2 are present in the sample. In an embodiment, the FGFR inhibitor is erdafitinib.

Disclosed herein are methods of treating cholangiocarcinoma in a patient harboring FGFR2-SBNO2 comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring FGFR2-SBNO2. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring FGFR2-SBNO2. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-SBNO2, wherein the presence of one or more FGFR mutants including at least FGFR2-SBNO2 is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2-SBNO2, wherein the presence of one or more FGFR mutants including at least FGFR2-SBNO2 is detected. In an embodiment, the FGFR inhibitor is erdafitinib.

In an embodiment of the invention, in the methods of treatment and the uses as described herein the FGFR2 SNP C383R may be replaced by the FGFR mutation FGFR2 C390>YS.

Disclosed herein are methods of treating cholangiocarcinoma in a patient comprising: evaluating a biological sample from the patient for the presence of one or more FGFR mutants including at least FGFR2 C390>YS; and treating the patient with an FGFR inhibitor if one or more FGFR mutants including at least FGFR2 C390>YS are present in the sample. In an embodiment, the FGFR inhibitor is erdafitinib.

Disclosed herein are methods of treating cholangiocarcinoma in a patient harboring FGFR2 C390>YS comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring FGFR2 C390>YS. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring FGFR2 C390>YS. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2 C390>YS, wherein the presence of one or more FGFR mutants including at least FGFR2 C390>YS is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2 C390>YS, wherein the presence of one or more FGFR mutants including at least FGFR2 C390>YS is detected. In an embodiment, the FGFR inhibitor is erdafitinib.

In an embodiment of the invention, in the methods of treatment and the uses as described herein the FGFR2 SNP C383R may be replaced by the FGFR mutation FGFR2 N549K.

Disclosed herein are methods of treating cholangiocarcinoma in a patient comprising: evaluating a biological sample from the patient for the presence of one or more FGFR mutants including at least FGFR2 N549K; and treating the patient with an FGFR inhibitor if one or more FGFR mutants including at least FGFR2 N549K are present in the sample. In an embodiment, the FGFR inhibitor is erdafitinib.

Disclosed herein are methods of treating cholangiocarcinoma in a patient harboring FGFR2 N549K comprising administering a FGFR inhibitor to said patient. The patient may comprise one or more further FGFR mutants. In an embodiment, the FGFR inhibitor is erdafitinib.

Disclosed herein is a FGFR inhibitor for use in the treatment of cholangiocarcinoma in a patient harboring FGFR2 N549K. The patient may comprise one or more further FGFR mutants. In an embodiment, the FGFR inhibitor is erdafitinib.

Disclosed herein is the use of a FGFR inhibitor in the manufacture of a medicament for the treatment of cholangiocarcinoma in a patient harboring FGFR2 N549K. The patient may comprise one or more further FGFR mutants. In an embodiment, the FGFR inhibitor is erdafitinib.

Disclosed herein is a FGFR inhibitor for use in the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2 N549K, wherein the presence of one or more FGFR mutants including at least FGFR2 N549K is detected. In an embodiment, the FGFR inhibitor is erdafitinib.

Disclosed herein is the use of a FGFR inhibitor for the manufacture of a medicament for the treatment of cholangiocarcinoma in a patient wherein the patient is identified as being responsive or likely to respond to the treatment with the FGFR inhibitor by evaluating a biological sample obtained from the patient for the presence of one or more FGFR mutants including at least FGFR2 N549K, wherein the presence of one or more FGFR mutants including at least FGFR2 N549K is detected. In an embodiment, the FGFR inhibitor is erdafitinib.

In an embodiment, the proportion of cholangiocarcinoma patients, in particular advanced cholangiocarcinoma patients, with at least one of the FGFR mutants as described herein showing objective response rate is at least 15%, or 20%, or 25%, or 30%, or 35%, or 40%, or 45%, or above 45%.

Methods of identification and analysis of FGFR mutants such as for example the FGFR2 SNP C383R can be performed using techniques known to a person skilled in the art and as described herein such as reverse-transcriptase polymerase chain reaction (RT-PCR) or in-situ hybridization such as fluorescence in situ hybridization (FISH). The diagnostic tests and screens are typically conducted on a biological sample selected from tumour biopsy samples, blood samples (isolation and enrichment of shed tumour cells), or as described hereinabove. The screening process will typically involve direct sequencing, oligonucleotide microarray analysis, or a mutant specific antibody.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Mutations and fusions are described herein with reference to the reference sequence NCBI Reference Sequence: NM_000141.4 and its corresponding amino acid sequence. FGFR2 C383R denotes an FGFR2 mutation in which cysteine in position 383 is replaced by arginine.

FGFR2 C390>YS describes an FGFR2 mutation in which cysteine in position 390 is replaced by tyrosine and serine.

FGFR2 N549K describes an FGFR2 mutation in which asparagine in position 549 is replaced by lysine.

FGFR2-KIAA1598 is a 5'-FGFR2 (ex1-17)-KIAA1598 (ex7-15)-3' fusion with REARR-POS1 chr10:123242270-123242562 and REARR-POS2 chr10:118709031-118709262 or with REARR-POS1 chr10:123242809-123243080 and REARR-POS2 chr10:118710247-118710599.

DTWD2-FGFR2 is a 5'-DTWD2(ex1)-FGFR2(ex18)-3' fusion with REARR-POS1 chr10:123242450-123242723 and REARR-POS2 chr5:118322151-118322550.

ESR2-FGFR2 is a 5'-ESR2 (ex1-3)-FGFR2 (ex18)-3' fusion with REARR-POS1 chr10:123239893-123240042 and REARR-POS2 chr14:64740210-64740315 FGFR2-MGEA5 is a 5'-FGFR2(ex1-17)-MGEA5(ex11-16)-3' fusion with REARR-POS1 chr10:123241032-123241358 and REARR-POS2 chr10:103557129-103557439. FGFR2-BICC1 is a 5'-FGFR2(ex1-17)-BICC1(ex3-21)-3' fusion with REARR-POS1 chr10:123242218-123242771 and REARR-POS2 chr10:60445416-60445560. FGFR2-SBNO2 is a 5'-FGFR2(x18)-SBNO2(x19-32)-3'fusion with REARR-POS1 chr10:123240725-123240921 and REARR-POS2 chr19:1113573-1113710.

EXAMPLES

1) Treatment of Patients with Cholangiocarcinoma

A clinical trial was conducted in which patients age ≥18 years were enrolled with advanced solid tumours for which standard curative therapy was no longer effective (NCT01703481; 4 part study).

Dose escalation (Part 1, all comers) followed a 3+3 design, with patients receiving ascending doses of erdafitinib at 0.5, 2, 4, 6, 9, and 12 mg QD (21-day cycles).

After daily dose escalation (Part 1), two intermittent doses were also evaluated at 10 and 12 mg 7 days on/7 days off (28-day cycles).

Subsequent parts (Parts 2-4) required documented FGFR-biomarker positive disease.

Part 2 (pharmacodynamics cohort, all comers) and Part 3 (dose-expansion cohort for recommended phase 2 dose of 9 mg QD, cholangiocarcinoma in addition to other cancers):

Tumors were required to be KRAS wild type and have any of the following: FGFR amplifications, FGFR activating mutations, FGFR translocations, or other aberrations of FGFR activation.

Part 4 (dose-expansion cohort for 10 mg intermittently, cholangiocarcinoma in addition to other cancers):

Tumors were required to have FGFR activating mutations or FGFR translocations.

Serial blood samples were collected to measure erdafinitib concentrations in plasma in Parts 1 and 2. Sparse samples were collected in Parts 3 and 4.

RESULTS

Eleven patients with FGFR-aberrant cholangiocarcinoma were treated at 9 mg QD (n=1, Part 3) or 10 mg intermittent (n=10, Part 4).

Of the 11 patients: 3 (27.3%) harbored FGFR mutations, and 8 (72.7%) harbored translocations.

Median treatment duration was 5.3 mo (range, 1 to 16 mo).

Patients received a median of 6 cycles (range, 2 to 17).

Most patients had received ≥6 cycles (8/11; 72.7%), including 4 (36.4%) treated with ≥9 cycles.

Systemic erdafitinib exposure in cholangiocarcinoma patients was similar to patients in all other cancer indications in this study.

Of the 3 partial responses, 1 patient had a FGFR mutation (FGFR2 C383R) and 2 had FGFR translocations (fusions of FGFR2-BICC1 [n=1] and FGFR2-CCAR1 [n=1]).

Overall disease control rate, including stable disease, was 54.5% (6/11).

With a median follow-up of 5.5 mo:

Median duration of response was 11.4 mo (95% CI, 9.9 to 12.9 mo).

Median progression-free survival was 5.1 mo (95% CI 1.6 to 11.8 mo).

6- and 9-mo progression-free survival rates were 36% and 24%, respectively.

As of the cutoff date, 1 patient continues on study treatment.

The objective response rate was 27.3% with a median duration of response of 11.4 months for erdafitinib 9 mg QD or 10 mg intermittent in this heavily pretreated population, with all responses seen at the latter dosing schedule.

The disease control rate was 54.5%.

Safety and PK data were consistent with those from the previously published results from Part 1 of this study (Tabernero J, et al: J Clin Oncol 33:3401-3408, 2015).

2) Treatment of Patients with Cholangiocarcinoma

A Study to evaluate the clinical efficacy of JNJ-42756493 (Erdafitinib), in Asian participants with advanced Non-Small-Cell Lung Cancer, Urothelial Cancer, Esophageal Cancer or Cholangiocarcinoma. (NCT02699606; LUC2001).

LUC2001 is an open-label, multicenter, phase 2a study including advanced cholangiocarcinoma subjects with FGFR alterations, based on FoundationOne testing, who failed at least 1 prior systemic treatment. The primary endpoint is objective response rate (ORR; by Response Evaluation Criteria in Solid Tumors (RECIST) version 1.1). The secondary endpoints are disease control rate (DCR), safety and pharmacokinetics. Disease is evaluated every 8 weeks until disease progression (PD). Participants receive 8 mg erdafitinib starting dose once daily with option to uptitrate to 9 mg on a 28-day cycle. The dose of the drug may be modified, delayed, or terminated based on guidelines in the protocol.

Inclusion Criteria:

Pathologically or cytologically confirmed, advanced or refractory tumors (there are no restriction on the total number of lines of prior therapies, but participant should have received at least 1 line of anti-cancer therapy [as per local standard of care]): Squamous and non-squamous non-small-cell lung cancer (NSCLC), esophageal cancer, urothelial cancer and cholangiocarcinoma Participants must meet the following molecular eligibility criteria (diagnosed at a central or local laboratory using either a tumor tissue based assay, which must indicate: at least one of following): a) fibroblast growth factor receptor (FGFR) gene translocations b) FGFR gene mutations that are considered activating c) Participants with evidence of FGFR pathway activation or other potential target/pathway inhibited by erdafitinib may also be considered and allowed for enrollment if supported by emerging biomarker data.

The presence of measurable disease according to the Response Evaluation Criteria in Solid Tumors (RECIST, Version 1.1) Criteria, and documented disease progression as defined by RECIST (Version 1.1) at baseline Eastern Cooperative Oncology Group (ECOG) performance status score 0 or 1

Female participants (of child bearing potential and sexually active) and male participants (with a partner of child bearing potential) must use medically acceptable methods of birth control. Male participants must use highly effective birth control measurements when sexually active and must not donate sperm Adequate bone marrow, liver, and renal function within the 14 days prior to Day 1 of Cycle 1 up until pre-dose of Cycle 1

Exclusion Criteria:

Chemotherapy, targeted therapies, immunotherapy, or treatment with an investigational anticancer agent within 2 weeks or at least 5 half-lives of the drug whichever is longer up to a maximum of 4 weeks before the first administration of study drug. Localized palliative radiation therapy (but should not include radiation to target lesions) and ongoing luteinizing hormone-releasing hormone (LHRH) agonists, bisphosphonates and denosumab, are permitted Participants with persistent phosphate greater than (>) upper limit of normal (ULN) during Screening (within 14 days prior to Day 1 of Cycle 1 up until pre-dose of Cycle 1) and despite medical management of phosphate levels Participants taking medications known to have a significant risk of causing QTc prolongation and Torsades de Pointes. Participants who have discontinued any of these medications must have a wash-out period of at least 5 days or at least 5 half-lives of the drug (whichever is longer) prior to the first dose of study drug Left ventricular ejection fraction (LVEF) less than (<) 50% as assessed by echocardiography (or multi-gated acquisition [MUGA]) performed at Screening Uncontrolled inter-current illness including, but not limited to, poorly controlled hypertension or diabetes, ongoing active infection requiring antibiotics, psychiatric illness, uncontrolled cardiovascular disease, or at risk of gastrointestinal perforation as per investigators' assessment Received prior selective FGFR inhibitor treatment or RET inhibitor treatment, respectively according to the biomarker prescreening result, or if the participant has known allergies, hypersensitivity, or intolerance to Erdafitinib or its excipients Any corneal or retinal abnormality likely to increase risk of eye toxicity All sexes Eligible for Study. Participants are 18 years and older.

Advanced cholangiocarcinoma patients who progressed after first-line chemotherapy have limited treatment options and poor prognosis.

Preliminary Results (Snapshot): As of 20 Mar. 2018, 150 advanced cholangiocarcinoma patients were molecularly screened and 25 had FGFR alterations, of whom 11 were dosed with 8 mg qd erdafitinib, all response evaluable. Median age was 53.0 years and ECOG score 0/1 in 6 and 5 subjects respectively. Median number of treatment cycles was 4.0 and median treatment duration was 3.5 months. There were 3 partial response (PR), 2 unconfirmed PR (uPR), 4 stable disease (SD), and 2 PD. The ORR (CR+PR+uCR+uPR) is 45.5%. The DCR (CR+PR+uCR+uPR+SD) is 81.8%. Six subjects are still on treatment. All subjects experienced AEs, 7 experienced Grade 3 or worse AEs, 3 experienced serious AEs (SAES) with no drug related SAE, all had AEs leading to drug interruption, 3 had AEs leading to dose reduction, while no AE led to treatment discontinuation or death. The most common AEs (>30%) were hyperphosphatemia (8/11), dry mouth (7/11), stomatitis (7/11), diarrhea (4/11), nail disorder (4/11), and palmar-plantar erythrodysaesthesia syndrome (4/11).

The participants with confirmed or unconfirmed partial response include participants with FGFR2-KIAA1598 and DTWD2-FGFR2 fusions, with ESR2-FGFR2 fusion, with FGFR2 C390>YS mutation and with FGFR2-MGEA5 fusion.

The participants with stable disease include participants with FGFR2-BICC1 fusion, with FGFR2 fusion with SBNO2 partner, with FGFR2 N549K mutation, and with FGFR2-KIAA1598 fusion.

Conclusion: PK characteristics are consistent with data from other erdafitinib studies. Erdafitinib showed encouraging clinical activity and tolerable safety profile in patients with FGFR-aberrant advanced cholangiocarcinoma.

The invention claimed is:

1. A method of treating cholangiocarcinoma in a patient comprising: evaluating a biological sample from the patient for the presence of one or more FGFR mutants; and treating the patient with erdafitinib if one or more FGFR mutants are present in the sample, wherein the dose of erdafitinib may be uptitrated depending on serum phosphate levels of the patient.

2. A method according to claim 1, wherein erdafitinib is administered at a dose of 8 mg, with an option to uptitrate to 9 mg depending on serum phosphate levels and depending on treatment-related adverse events observed, wherein the levels of serum phosphate for determining whether or not to up-titrate are measured on a treatment day during the first cycle of erdafitinib treatment.

3. A method according to claim 2, wherein the dose of erdafitinib is uptitrated to 9 mg when the serum phosphate levels are <5.5 mg/dL, or are <7 mg/dL or range from and include 7 mg/dL to ≤9 mg/dL or are ≤9 mg/dL.

4. A method according to claim 3, wherein the dose of erdafitinib is uptitrated to 9 mg when the serum phosphate levels are <5.5 mg/dL.

5. A method according to claim 3, wherein the dose of erdafitinib is uptitrated to 9 mg when the serum phosphate levels are <7 mg/dL.

6. A method according to claim 3, wherein the dose of erdafitinib is uptitrated to 9 mg when the serum phosphate levels range from and include 7 mg/dL to ≤9 mg/dL.

7. A method according to claim 3, wherein the dose of erdafitinib is uptitrated to 9 mg when the serum phosphate levels are ≤9 mg/dL.

8. A method according to claim 2, wherein the levels of serum phosphate for determining whether or not to up-titrate are measured on day 14±2 days of erdafitinib administration.

9. A method according to claim 5, wherein the levels of serum phosphate for determining whether or not to up-titrate are measured on day 14±2 days of erdafitinib administration.

10. A method according to claim 7, wherein the levels of serum phosphate for determining whether or not to up-titrate are measured on day 14±2 days of erdafitinib administration.

11. A method according to claim 8, wherein the levels of serum phosphate for determining whether or not to up-titrate are measured on day 14 of erdafitinib administration.

12. A method according to claim 1, wherein the one or more FGFR mutants are selected from FGFR2 SNP C383R; FGFR2-BICC1; FGFR2-CCAR1; FGFR2-KIAA1598; DTWD2-FGFR2; ESR2-FGFR2; FGFR2-MGEA5; FGFR2-SBNO2; or FGFR2 C390>YS.

13. A method according to claim 12, wherein the one or more FGFR mutants is FGFR2-BICC1.

14. A method according to claim 12, wherein the one or more FGFR mutants is FGFR2-CCAR1.

15. A method according to claim 12, wherein the one or more FGFR mutants is FGFR2-KIAA1598.

16. A method according to claim 12, wherein the one or more FGFR mutants is DTWD2-FGFR2.

17. A method according to claim 12, wherein the one or more FGFR mutants is ESR2-FGFR2.

18. A method according to claim 12, wherein the one or more FGFR mutants is FGFR2-MGEA5.

19. A method according to claim 12, wherein the one or more FGFR mutants is FGFR2-SBNO2.

20. A method according to claim 2, wherein the erdafitinib is administered at a dose of 8 mg once daily.

* * * * *